United States Patent
Minas et al.

(10) Patent No.: US 11,622,746 B2
(45) Date of Patent: Apr. 11, 2023

(54) INTRALUMINAL IMAGING DEVICE WITH WIRE INTERCONNECTION FOR IMAGING ASSEMBLY

(71) Applicant: KONINKLIJKE PHILIPS N.V., Eindhoven (NL)

(72) Inventors: Maritess Minas, San Diego, CA (US); Princeton Saroha, Ladera Ranch, CA (US); Jeremy Stigall, Carlsbad, CA (US); David Kenneth Wrolstad, Fallbrook, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 175 days.

(21) Appl. No.: 16/482,039

(22) PCT Filed: Feb. 5, 2018

(86) PCT No.: PCT/EP2018/052760
§ 371 (c)(1),
(2) Date: Jul. 30, 2019

(87) PCT Pub. No.: WO2018/141949
PCT Pub. Date: Aug. 9, 2018

(65) Prior Publication Data
US 2019/0388055 A1 Dec. 26, 2019

Related U.S. Application Data

(60) Provisional application No. 62/455,127, filed on Feb. 6, 2017.

(51) Int. Cl.
*A61B 8/00* (2006.01)
*A61B 8/12* (2006.01)

(52) U.S. Cl.
CPC ............... *A61B 8/12* (2013.01); *A61B 8/445* (2013.01); *A61B 8/4488* (2013.01);
(Continued)

(58) Field of Classification Search
CPC ......... A61B 8/12; A61B 8/445; A61B 8/4488; A61B 8/4494; A61B 8/54; A61B 2562/12; A61B 8/0891
See application file for complete search history.

(56) References Cited

U.S. PATENT DOCUMENTS 5,735,282 A 4/1998 Hossack
6,004,269 A * 12/1999 Crowley .............. A61B 8/4461
600/374

(Continued)

FOREIGN PATENT DOCUMENTS

EP 0671221 A2 9/1995
WO 2017001525 A1 1/2017

*Primary Examiner* — Pascal M Bui Pho
*Assistant Examiner* — Taylor Deutsch

(57) ABSTRACT

An intraluminal imaging device includes a flexible elongate member configured to be inserted into a lumen within a body of a patient, the flexible elongate member comprising a longitudinal axis; an imaging assembly coupled to the flexible elongate member, the imaging assembly comprising: a plurality of ultrasound transducer elements disposed around the longitudinal axis of the flexible elongate member; a plurality of controllers configured to control the plurality of ultrasound transducer elements to obtain imaging data associated with the lumen; and a plurality of electrical wires extending between the plurality of the ultrasound transducer elements and the plurality of controllers and configured to facilitate communication between the plurality of the ultrasound transducer elements and the plurality of controllers.

21 Claims, 12 Drawing Sheets

(52) U.S. Cl.
CPC .............. *A61B 8/4494* (2013.01); *A61B 8/54* (2013.01); *A61B 2562/12* (2013.01)

(56) References Cited

U.S. PATENT DOCUMENTS

| | | | |
|---|---|---|---|
| 6,120,516 A * | 9/2000 | Selmon | A61B 1/00179 |
| | | | 606/159 |
| 6,641,540 B2 | 11/2003 | Fleischman | |
| 6,776,763 B2 | 8/2004 | Nix | |
| 7,226,417 B1 | 6/2007 | Eberle et al. | |
| 7,846,101 B2 | 12/2010 | Eberle et al. | |
| 2003/0229286 A1 | 12/2003 | Lenker | |
| 2013/0331706 A1* | 12/2013 | Hossack | A61B 8/445 |
| | | | 600/467 |
| 2014/0180118 A1 | 6/2014 | Stigall | |
| 2014/0180124 A1* | 6/2014 | Whiseant | A61B 8/0891 |
| | | | 600/467 |
| 2014/0187960 A1 | 7/2014 | Corl | |
| 2014/0257107 A1* | 9/2014 | Rice | A61B 8/4483 |
| | | | 600/459 |
| 2015/0216550 A1* | 8/2015 | Richter | A61B 17/3207 |
| | | | 606/159 |
| 2015/0305710 A1 | 10/2015 | Stigall et al. | |
| 2015/0305716 A1* | 10/2015 | Rice | A61B 8/4461 |
| | | | 600/445 |
| 2016/0007962 A1 | 1/2016 | Esbeck | |
| 2016/0081657 A1 | 3/2016 | Rice | |

\* cited by examiner

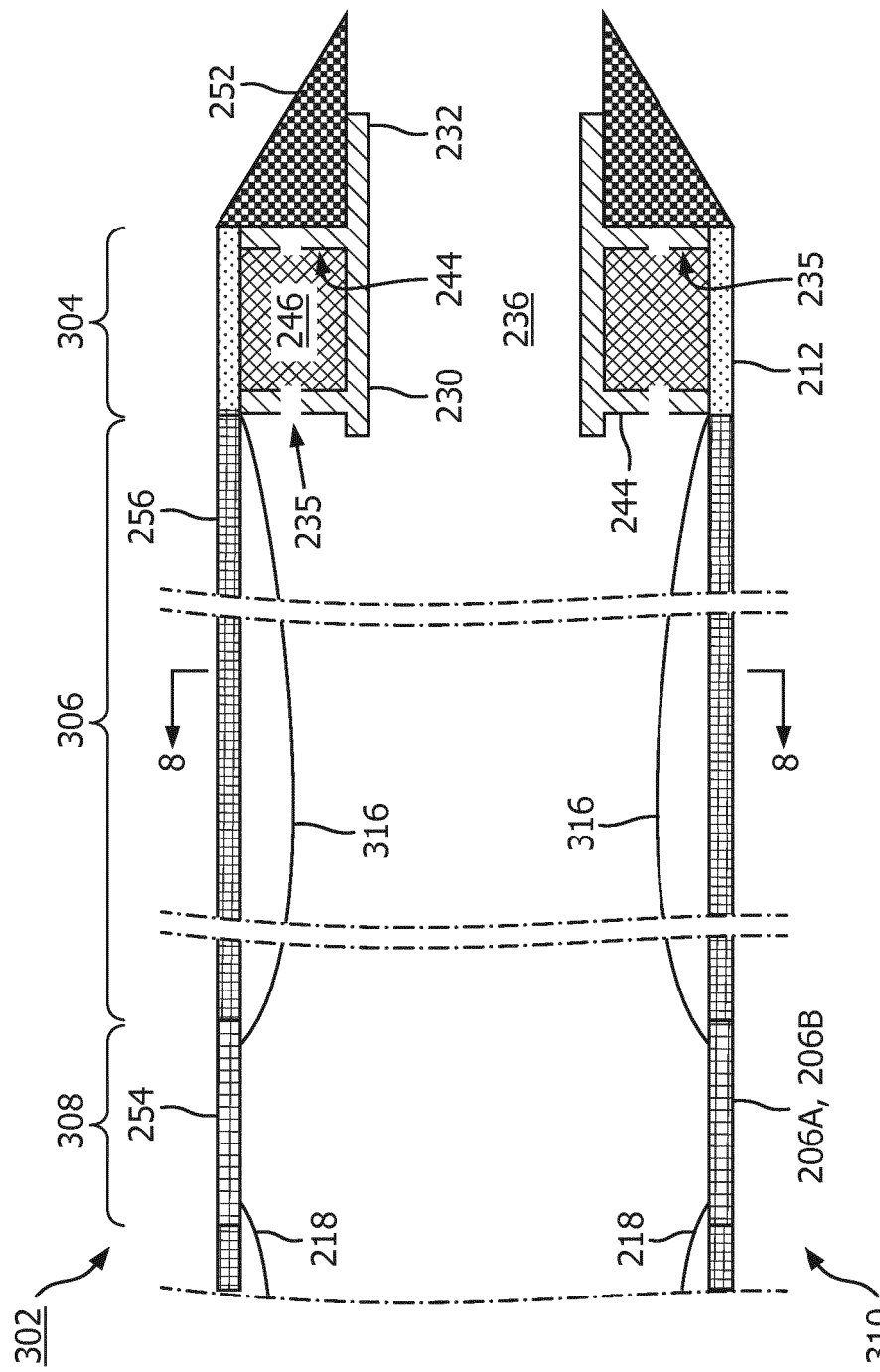

INTRALUMINAL IMAGING DEVICE WITH WIRE INTERCONNECTION FOR IMAGING ASSEMBLY

TECHNICAL FIELD

The present disclosure relates generally to array-based intraluminal imaging, such as phased array intravascular ultrasound (IVUS) imaging. In particular, a flexible structure using a plurality of electrical cables for an imaging assembly is described.

BACKGROUND

Intravascular imaging is widely used in interventional cardiology as a diagnostic tool for assessing a diseased vessel, such as an artery, within the human body to determine the need for treatment, to guide the intervention, and/or to assess its effectiveness. An intravascular imaging device including one or more ultrasound transducers is passed into the vessel and guided to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an intravascular imaging system. The imaging system processes the received ultrasound echoes to produce a cross-sectional image of the vessel where the device is placed.

Solid-state (also known as synthetic-aperture) intravascular imaging catheters are one of the two types of intravascular imaging devices commonly used today, the other type being the rotational intravascular imaging catheter. Solid-state intravascular imaging catheters carry a scanner assembly that includes an array of ultrasound transducers distributed around its circumference along with one or more integrated circuit controller chips mounted adjacent to the transducer array. The controllers select individual transducer elements (or groups of elements) for transmitting an ultrasound pulse and for receiving the ultrasound echo signal. By stepping through a sequence of transmit-receive pairs, the solid-state intravascular imaging system can synthesize the effect of a mechanically scanned ultrasound transducer but without moving parts (hence the solid-state designation). Since there is no rotating mechanical element, the transducer array can be placed in direct contact with the blood and close to the vessel tissue with minimal risk of vessel trauma. Furthermore, because there is no rotating element, the electrical interface is simplified. The solid-state scanner can be wired directly to the imaging system with a simple electrical cable and a standard detachable electrical connector, rather than the complex rotating electrical interface required for a rotational intravascular imaging device.

Manufacturing an intraluminal imaging device that can efficiently traverse physiology within the human body is challenging. In that regard, some IVUS devices utilize an imaging assembly having controllers and transducers as part of a single substrate. The substrate and the transducers and controllers formed on the substrate create an area of high rigidity at the distal portion of the intravascular imaging device. Areas of high rigidity increase the likelihood of kinking as the intravascular imaging device is steered through vasculature.

SUMMARY

The present invention provides an intraluminal ultrasound imaging system that overcomes the limitations of a rigid imaging assembly while achieving efficient assembly and operation.

Embodiments of the present disclosure provide an improved intraluminal imaging system for generating images of a lumen within the body of a patient, such as a blood vessel. An imaging assembly of the imaging device includes electrical wires extending between electronic controllers and transducers. For example, the controllers can be formed on a first flexible substrate and the transducers can be formed on a second flexible substrate. A tubular member that is made of a more flexible material than the substrates can extend between the two flexible substrates. By implementing the electrical wires and more flexible tubular member between the controllers and transducers, rather than a single, stiff substrate as in earlier devices, the imaging assemblies described herein have a reduced length of rigidity. A backing material and a support member may only extend under the transducers, in contrast to under both the controllers and transducer in previous devices, which further reduces the stiff length of the imaging assembly. The limited extent of the support member, using electrical wires, and the more flexible tubular member between the two substrates provide more flexibility than previous imaging assemblies. In that regard, by implementing electrical wires, the rigid length associated with the support member of the imaging assembly is shortened to include only the region of the transducers. The electrical wires extend along the length between the controllers and transducers. Because of the reduced stiff length associated with the imaging assembly, the intravascular device can be steered through the lumen within the patient body more efficiently and with less risk of kinking.

In one embodiment, an intraluminal imaging device is provided. The intraluminal imaging device includes a flexible elongate member that may be inserted into a lumen within a body of a patient. The flexible elongate member may comprise a longitudinal axis. The intraluminal imaging device also includes an imaging assembly that is coupled to the flexible elongate member. The imaging assembly comprises a plurality of ultrasound transducer elements that are disposed around the longitudinal axis of the flexible elongate member. The imaging assembly also includes a plurality of controllers that may control the plurality of ultrasound transducer elements to obtain imaging data associated with the lumen. The imaging assembly further includes a plurality of electrical wires, e.g., micro-wires that may extend between the plurality of the ultrasound transducer elements and the plurality of controllers and may facilitate communication between the plurality of the transducers and the plurality of controllers.

In some embodiments, the plurality of electrical wires may be divided into a plurality of bundles each having multiple electrical wires of the plurality of electrical wires. In some embodiments, the intraluminal imaging device further includes a steering wire for deflecting the distal portion of the flexible elongate member. The steering wire is positioned in a space between the bundles within the flexible elongate member. In some examples, a quantity of the plurality of ultrasound transducer elements equals a quantity of the plurality of electrical wires.

In some embodiments, the intraluminal imaging device further includes a first flexible substrate, e.g., a first flex circuit, where the plurality of ultrasound transducer elements are formed on the first flexible substrate and a second flexible substrate, e.g., a second flex circuit, where the plurality of controllers are formed on the second flexible substrate. The plurality of electrical wires may extend between the first and second flexible substrates.

In one embodiment, a method of assembling an intraluminal imaging device is provided. The method includes positioning a plurality of ultrasound transducer elements around a longitudinal axis of a flexible elongate member configured to be inserted into a lumen within a body of a patient. The method also includes positioning a plurality of controllers around the longitudinal axis of the flexible elongate member. The method includes establishing electrical communication between the plurality of controllers and the plurality of ultrasound transducer elements by extending a plurality of electrical wires between the plurality of the ultrasound transducer elements and the plurality of the controllers.

In some embodiments, the method further includes dividing the plurality of electrical wires into a plurality of bundles such that each bundle may comprise multiple electrical wires. The plurality of bundles may extend between the plurality of the ultrasound transducer elements and the plurality of controllers.

In some embodiments, an imaging system is provided. The imaging system includes an intraluminal imaging device. The intraluminal imaging device includes a flexible elongate member that may be inserted into a lumen within a body of a patient. The flexible elongate member may comprise a longitudinal axis. The intraluminal imaging device also includes an imaging assembly that is coupled to the flexible elongate member. The imaging assembly comprises a plurality of ultrasound transducer elements that are disposed around the longitudinal axis of the flexible elongate member. The imaging assembly also includes a plurality of controllers that may control the plurality of ultrasound transducer elements and may obtain imaging data associated with the lumen. The imaging assembly further includes a plurality of electrical wires, e.g., micro-wires that may extend between the plurality of the ultrasound transducer elements and the plurality of controllers and may facilitate communication between the plurality of the transducers and the plurality of controllers. The imaging system also includes a computing device in communication with the intraluminal imaging device. The computing device may process the imaging data received from the intraluminal imaging device and may output the processed imaging data to a display.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 4C is a diagrammatic cross-sectional side view of an intravascular device including an imaging assembly, according to aspects of the present disclosure.

DETAILED DESCRIPTION

Figure 1:
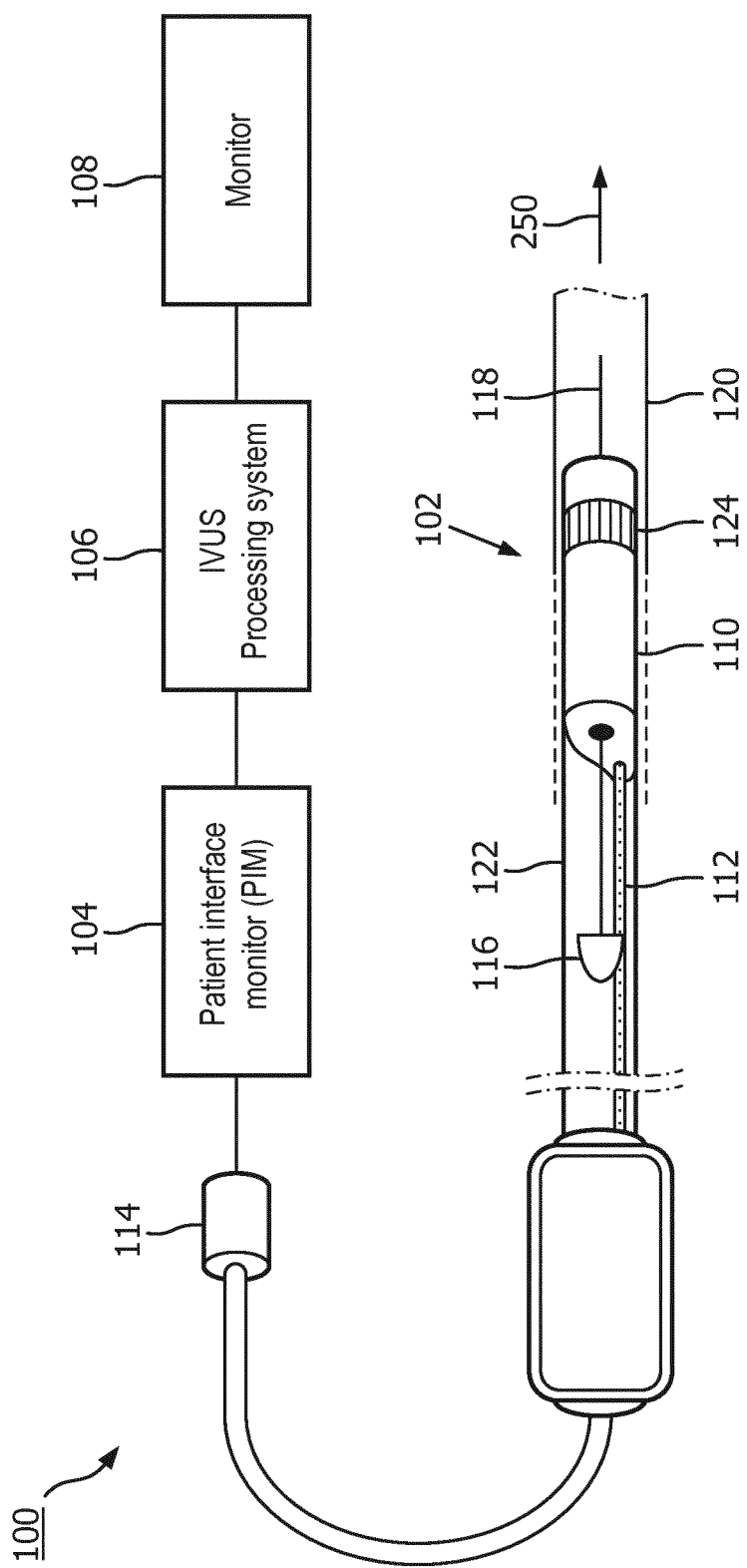
FIG. 1 is a diagrammatic schematic view of an imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the focusing system is described in terms of cardiovascular imaging, it is understood that it is not intended to be limited to this application. The system is equally well suited to any application requiring imaging within a confined cavity. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an intraluminal imaging system 100, according to aspects of the present disclosure. The intraluminal imaging system 100 may include a solid-state or phased array intraluminal imaging device 102 such as a catheter, guide wire, or guide catheter, a patient interface module (PIM) 104, an image processing system or console 106, and a monitor 108.

Figure 2:
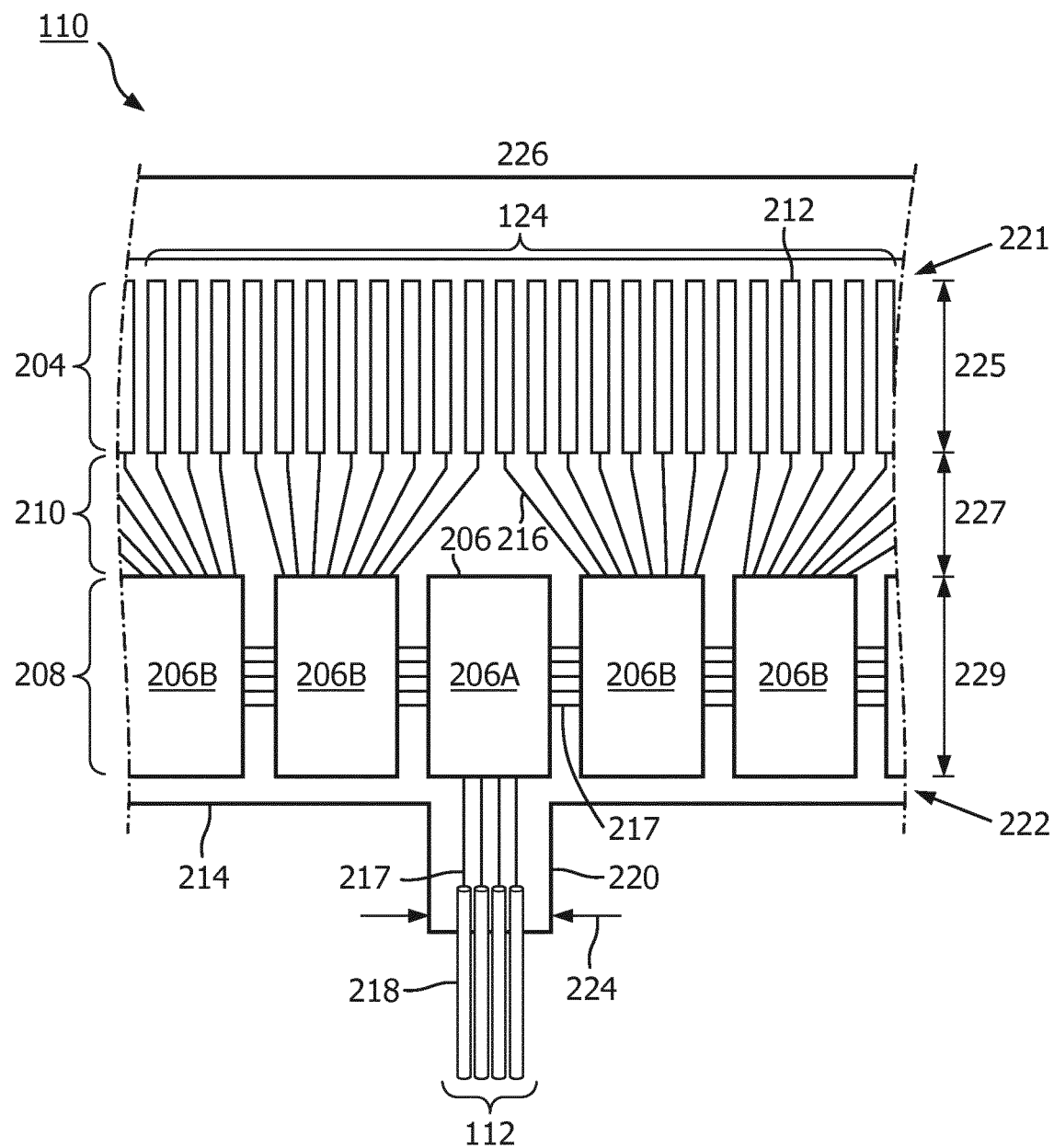
FIG. 2 is a diagrammatic top view of a scanner assembly in a flat configuration, according to aspects of the present disclosure.

The intraluminal imaging device 102 includes a flexible elongate member 122 that is configured to be inserted into a lumen, e.g., a vessel 120, within a body of a patient. The flexible elongate member 122 can include one or more elongate members that are formed a flexible material, such as a plastic or a polymer. The flexible elongate member 122 can have generally tubular shape with a circular cross-sectional profile. In some embodiments, an inner tubular member can be concentrically positioned within an outer tubular member. The flexible elongate member 122 may include a proximal portion, a central portion, a distal portion, and a longitudinal axis. A connector 114 can be disposed at the proximal portion of the flexible elongate member. The central portion extends between the proximal portion and the distal portion. A scanner assembly or imaging assembly 110 can be disposed at the distal portion of the flexible elongate member 122. As shown in FIG. 2, the scanner assembly 110 includes controllers 206A, 206B in communication with transducer elements 212 of the array 124.

At a high level, the intraluminal imaging device 102 emits ultrasonic energy from a transducer array 124 included in scanner assembly 110 mounted near a distal end of the catheter device. The ultrasonic energy is reflected by tissue structures in the medium, such as a vessel 120, surrounding the scanner assembly 110, and the ultrasound echo signals are received by the transducer array 124. The PIM 104 transfers the received echo signals to the console or computer 106 where the ultrasound image is reconstructed and displayed on the monitor 108. The console 106 or computer can include one or more processors and any suitable memory. The computer or console 106 can be operable to facilitate the features of the intraluminal imaging system 100 described herein. For example, the processor can execute computer readable instructions stored on the non-transitory tangible computer readable medium.

The PIM 104 facilitates communication of signals between the computing device 106 and the scanner assembly 110 included in the imaging device 102. The communication of signals among the computing device 106, PIM 104, and the scanner assembly 110 includes: (1) providing commands to integrated circuit controller chip(s) 206A, 206B (FIG. 2) to select the particular transducer array element(s) 212 to be used for transmit and receive, (2) providing the transmit trigger signals to the integrated circuit controller chip(s) 206A, 206B to activate the transmitter circuitry to generate an electrical pulse to excite the selected transducer array element(s), and/or (3) accepting amplified echo signals received from the selected transducer array element(s) via amplifiers included on the integrated circuit controller chip(s) 206 of the scanner assembly 110. In some embodiments, the PIM 104 performs preliminary processing of the echo data prior to relaying the data to the console 106. In examples of such embodiments, the PIM 104 performs amplification, filtering, and/or aggregating of the data. In an embodiment, the PIM 104 also supplies high- and low-voltage DC power to support operation of the imaging device 102 including circuitry within the scanner assembly 110.

The intraluminal imaging console 106 receives the echo data from the scanner assembly 110 by way of the PIM 104 and processes the data to reconstruct an image of the tissue structures in the medium surrounding the scanner assembly 110. The console 106 outputs image data such that an image of the vessel 120, such as a cross-sectional image of the vessel 120, is displayed on the monitor 108. Vessel 120 may represent fluid filled or surrounded structures, both natural and man-made. The vessel 120 may be within a body of a patient. The vessel 120 may be a blood vessel, as an artery or a vein of a patient's vascular system, including cardiac vasculature, peripheral vasculature, neural vasculature, renal vasculature, and/or any suitable lumen inside the body. The imaging device 102 is an intravascular imaging device or IVUS imaging device in some embodiments. The imaging device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the imaging device 102 may be used to examine man-made structures such as, but without limitation, heart valves, stents, shunts, filters and other devices.

In some embodiments, the intraluminal imaging device includes some features similar to traditional solid-state intravascular imaging catheters, such as the EagleEye® catheter available from Volcano Corporation and those disclosed in U.S. Pat. No. 7,846,101 hereby incorporated by reference in its entirety. For example, the intraluminal imaging device 102 includes the scanner assembly 110 near a distal end of the imaging device 102 and a transmission line cable 112 extending along the longitudinal body of the imaging device 102. The transmission line bundle or cable 112 can include a plurality of conductors, including one, two, three, four, five, six, seven, or more conductors 218 (FIG. 2). It is understood that any suitable gauge wire can be used for the conductors 218. In an embodiment, the cable 112 can include a four-conductor transmission line arrangement with, e.g., 41 AWG gauge wires. In an embodiment, the cable 112 can include a seven-conductor transmission line arrangement utilizing, e.g., 44 AWG gauge wires. In some embodiments, 43 AWG gauge wires can be used. The conductors 218 facilitate communication of electrical signals between the imaging assembly 110 and the computing device 106.

The transmission line cable 112 terminates in a PIM connector 114 at a proximal end of the imaging device 102. The PIM connector 114 electrically couples the transmission line cable 112 to the PIM 104 and physically couples the intraluminal imaging device 102 to the PIM 104. In an embodiment, the intraluminal imaging device 102 further includes a guide wire exit port 116. Accordingly, in some instances the intraluminal imaging device is a rapid-exchange catheter. The guide wire exit port 116 allows a guide wire 118 to be inserted towards the distal end in order to direct the imaging device 102 through the vessel 120.

Figure 3:
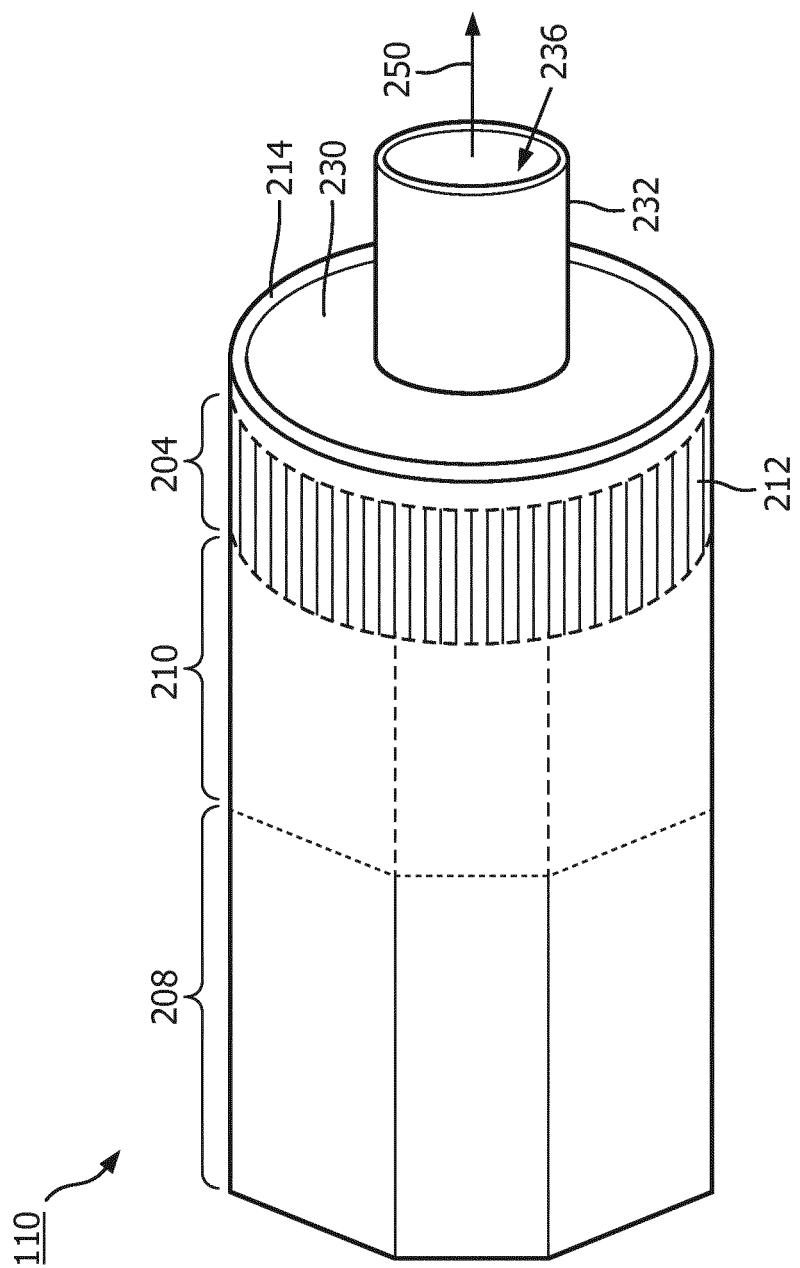
FIG. 3 is a diagrammatic side view of a scanner assembly in a rolled configuration around a support member for the transducers, according to aspects of the present disclosure.

FIG. 2 is a top view of a portion of an ultrasound scanner assembly 110 according to an embodiment of the present disclosure. The scanner assembly 110 includes a transducer array 124 formed in a transducer region 204 and transducer control logic dies 206 (including dies 206A and 206B) formed in a control region 208, with a transition region 210 disposed therebetween. The transducer control logic dies 206 and the transducers 212 are mounted on a flexible substrate 214 that is shown in a flat configuration in FIG. 2. A rolled or cylindrical configuration of the imaging assembly 110 is illustrated in FIG. 3. The transducer array 124 is a non-limiting example of a medical sensor element and/or a medical sensor element array. The transducer control logic dies 206 is a non-limiting example of a control circuit. The transducer region 204 is disposed adjacent a distal portion 221 of the flexible substrate 214. The control region 208 is disposed adjacent the proximal portion 222 of the flexible substrate 214. The transition region 210 is disposed between the control region 208 and the transducer region 204. Dimensions of the transducer region 204, the control region 208, and the transition region 210 (e.g., lengths 225, 227, 229) can vary in different embodiments.

The transducer array 124 may include any number and type of ultrasound transducers 212, although for clarity only a limited number of ultrasound transducers are illustrated in FIG. 2. In an embodiment, the transducer array 124 may include 64 individual ultrasound transducers 212. In a further embodiment, the transducer array 124 may include 32 ultrasound transducers 212. Other numbers are both contemplated and provided for. With respect to the types of transducers, in an embodiment, the ultrasound transducers of the transducer array 124 are piezoelectric micromachined ultrasound transducers (PMUTs) fabricated on a microelectromechanical system (MEMS) substrate using a polymer piezoelectric material, for example as disclosed in U.S. Pat. No. 6,641,540, which is hereby incorporated by reference in its entirety. In alternate embodiments, the transducer array includes piezoelectric zirconate transducers (PZT) transducers such as bulk PZT transducers, capacitive micromachined ultrasound transducers (cMUTs), single crystal piezoelectric materials, other suitable ultrasound transmitters and receivers, and/or combinations thereof.

The scanner assembly 110 may include various transducer control logic, which in the illustrated embodiment is divided into discrete control logic dies 206. In various examples, the control logic of the scanner assembly 110 performs: decoding control signals sent by the PIM 104 across the cable 112, driving one or more transducers 212 to emit an ultrasonic signal, selecting one or more transducers 212 to receive a reflected echo of the ultrasonic signal, amplifying a signal representing the received echo, and/or transmitting the signal to the PIM across the cable 112. In the illustrated embodiment, a scanner assembly 110 having 64 ultrasound transducers 212 divides the control logic across nine control logic dies 206, of which five are shown in FIG. 2. Designs incorporating other numbers of control logic dies 206 including 8, 9, 16, 17 and more are utilized in other embodiments. In general, the control logic dies 206 are characterized by the number of transducers they are capable of driving, and exemplary control logic dies 206 drive 4, 8, and/or 16 transducers.

The control logic dies are not necessarily homogenous. In some embodiments, a single controller is designated a master control logic die 206A and contains the communication interface for the cable 112. Accordingly, the master control circuit may include control logic that decodes control signals received over the cable 112, transmits control responses over the cable 112, amplifies echo signals, and/or transmits the echo signals over the cable 112. The remaining controllers are slave controllers 206B. The slave controllers 206B may include control logic that drives a transducer 212 to emit an ultrasonic signal and selects a transducer 212 to receive an echo. In the depicted embodiment, the master controller 206A does not directly control any transducers 212. In other embodiments, the master controller 206A drives the same number of transducers 212 as the slave controllers 206B or drives a reduced set of transducers 212 as compared to the slave controllers 206B. In an exemplary embodiment, a single master controller 206A and eight slave controllers 206B are provided with eight transducers assigned to each slave controller 206B.

The flexible substrate 214, on which the transducer control logic dies 206 and the transducers 212 are mounted, provides structural support and interconnects for electrical coupling. The flexible substrate 214 may be constructed to include a film layer of a flexible polyimide material such as KAPTON™ (trademark of DuPont). Other suitable materials include polyester films, polyimide films, polyethylene napthalate films, or polyetherimide films, other flexible printed semiconductor substrates as well as products such as Upilex® (registered trademark of Ube Industries) and TEFLON® (registered trademark of E.I. du Pont). In the flat configuration illustrated in FIG. 2, the flexible substrate 214 has a generally rectangular shape. As shown and described herein, a distal portion of the flexible substrate 214 is configured to be wrapped around a support member 230 (FIGS. 3 and 4A) to form a cylindrical toroid in some instances. Therefore, the thickness of the film layer of the flexible substrate 214 is generally related to the degree of curvature in the final assembled scanner assembly 110. In some embodiments, the film layer is between 5 µm and 100 µm, with some particular embodiments being between 12.7 µm and 25.1 µm.

Referring again to FIG. 2, to electrically interconnect the control logic dies 206 and the transducers 212, in an embodiment, the flexible substrate 214 further includes conductive traces 216, 217 formed on the film layer or under the film layer inside the lumen 238 that carry signals between the control logic dies 206 and the transducers 212. In particular, the conductive traces 216 providing communication between the control logic dies 206 and the transducers 212 extend along the flexible substrate 214 within the transition region 210. In some instances, in the region 208, conductive traces 217 can facilitate electrical communication between the master controller 206A and the slave controllers 206B. The conductive traces 217 can also provide a set of conductive pads that contact the conductors 218 of cable 112 when the conductors 218 of the cable 112 are mechanically and electrically coupled to the flexible substrate 214. Suitable materials for the conductive traces 216, 217 include copper, gold, aluminum, silver, tantalum, nickel, and tin, and may be deposited on the flexible substrate 214 by processes such as sputtering, plating, and etching. In an embodiment, the flexible substrate 214 includes a chromium adhesion layer. The width and thickness of the conductive traces 216, 217 are selected to provide proper conductivity and resilience when the flexible substrate 214 is rolled. In that regard, an exemplary range for the thickness of a conductive trace 216, 217 and/or conductive pad is between 10-50 µm. For example, in an embodiment, 20 µm conductive traces 216, 217 are separated by 20 µm of space. The width of a conductive trace 216, 217 on the flexible substrate 214 may be further determined by the width of the conductor 218 to be coupled to the trace/pad. In some examples, in place of the conductive traces, conductive traces 216 are formed on top the film layer of the flexible substrate 214.

As described herein, in some embodiments, the flexible substrate 214 within the transition region 210 is omitted. In such embodiments, a plurality of electrical wires extend between the controllers 206A, 206B and the transducers 212 to facilitate electrical communication there between. The electrical wires can be positioned within the flexible elongate member 122.

Referring again to FIG. 2, the flexible substrate 214 can include a conductor interface 220 in some embodiments. The conductor interface 220 can be a location of the flexible substrate 214 where the conductors 218 of the cable 112 are coupled to the flexible substrate 214. For example, the bare conductors of the cable 112 are electrically coupled to the flexible substrate 214 at the conductor interface 220. The conductor interface 220 can be tab extending from the main body of flexible substrate 214. In that regard, the main body of the flexible substrate 214 can refer collectively to the transducer region 204, controller region 208, and the transition region 210. In the illustrated embodiment, the conductor interface 220 extends from the proximal portion 222 of the flexible substrate 214. In other embodiments, the conductor interface 220 is positioned at other parts of the flexible substrate 214, such as the distal portion 221, or the flexible substrate 214 omits the conductor interface 220. A value of a dimension of the tab or conductor interface 220, such as a width 224, can be less than the value of a dimension of the main body of the flexible substrate 214, such as a width 226. In some embodiments, the substrate forming the conductor interface 220 is made of the same material(s) and/or is similarly flexible as the flexible substrate 214. In other embodiments, the conductor interface 220 is made of different materials and/or is comparatively more rigid than the flexible substrate 214. For example, the conductor interface 220 can be made of a plastic, thermoplastic, polymer, hard polymer, etc., including polyoxymethylene (e.g., DELRIN®), polyether ether ketone (PEEK), nylon, and/or other suitable materials. As described in greater detail herein, the support member 230, the flexible substrate 214, the conductor interface 220 and/or the conductor(s) 218 can be variously configured to facilitate efficient manufacturing and operation of the scanner assembly 110.

FIG. 3 is a diagrammatic side view of the imaging assembly 110 in the rolled configuration around the support member 230, according to aspects of the present disclosure. While the scanner assembly 110 of FIGS. 2 and 3 are described as including a flexible substrate, it is understood that the transducers and/or controllers may be arranged to form the scanner assembly 110 in other configurations, including those omitting a flexible substrate. Referring to FIGS. 1 and 3, in some embodiments, the imaging assembly 110 may include a plurality of ultrasound transducer elements 212 disposed in an annular configuration, for example, in a circular or in a polygon configuration, around the longitudinal axis 250 of the flexible elongate member 122. For example, any suitable annular polygon shape can be implemented, such as a based on the number of transducers, flexibility of the transducers, etc., including a hexagon, heptagon, octagon, nonagon, decagon, etc. In some examples, the imaging assembly 110 further includes a plurality of controllers 206A, 206B for controlling the plurality of ultrasound transducer elements 212 to obtain imaging data associated with the vessel 120. The plurality of controllers 206A, 206B can be positioned around the longitudinal axis 250, such as in an annular configuration, for example, in a circular or in a polygon configuration. For example, any suitable annular polygon shape can be implemented, such as a based on the number of controllers, flexibility of the controllers, etc., including a hexagon, heptagon, octagon, nonagon, decagon, etc.

Figure 4A:
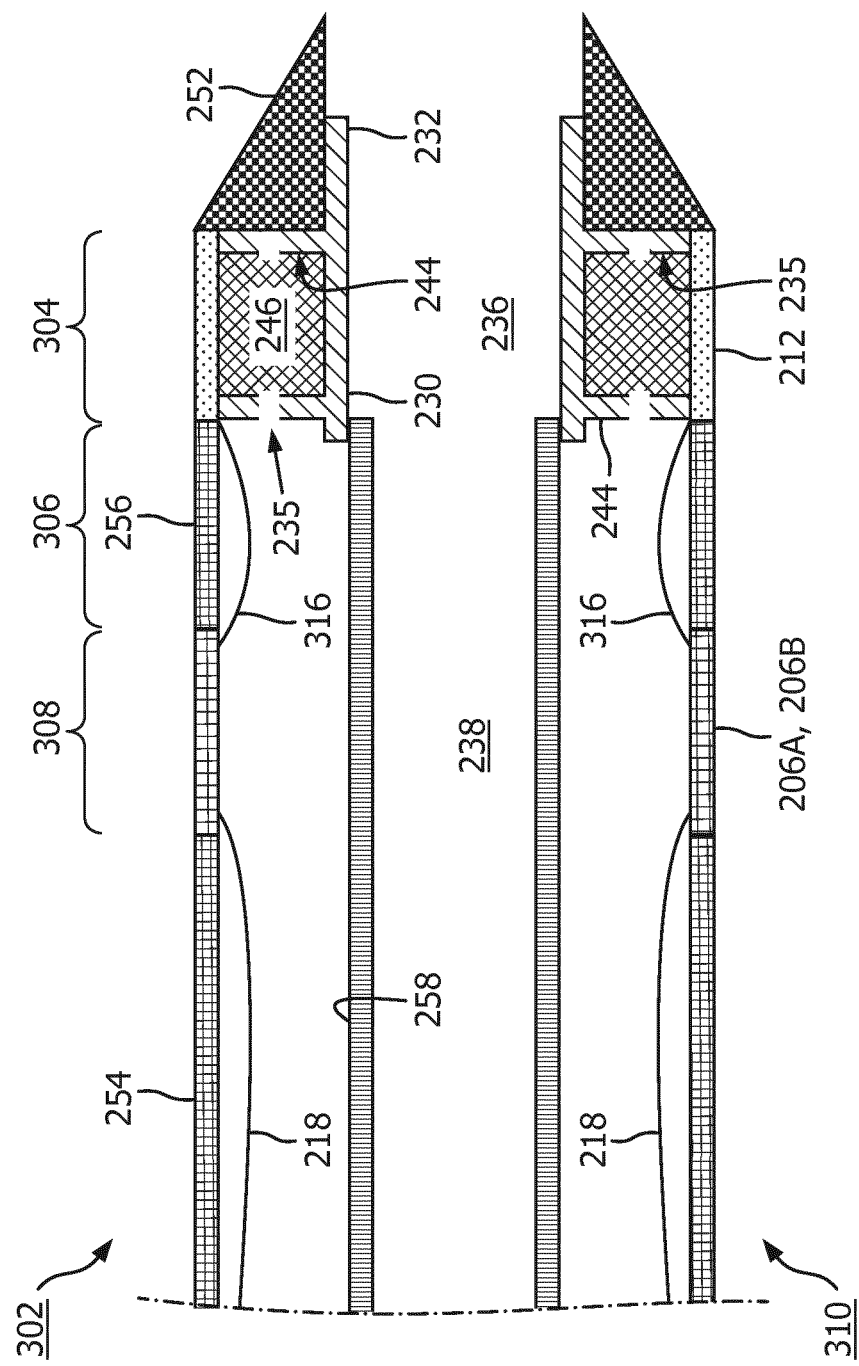
FIG. 4A is a diagrammatic cross-sectional side view of an intravascular device including an imaging assembly, according to aspects of the present disclosure.

In some instances, the scanner assembly 110 is transitioned from a flat configuration (FIG. 2) to a rolled or more cylindrical configuration (FIGS. 3 and 4A). For example, in some embodiments, techniques are utilized as disclosed in one or more of U.S. Pat. No. 6,776,763, titled "ULTRASONIC TRANSDUCER ARRAY AND METHOD OF MANUFACTURING THE SAME" and U.S. Pat. No. 7,226,417, titled "HIGH RESOLUTION INTRAVASCULAR ULTRASOUND TRANSDUCER ASSEMBLY HAVING A FLEXIBLE SUBSTRATE," each of which is hereby incorporated by reference in its entirety.

FIG. 4A is a diagrammatic cross-sectional side view of an imaging device 302 including an imaging assembly 310. The imaging device 302 and the imaging assembly 310 can include features similar to those described with respect to the imaging device 102 and the imaging assembly 110, respectively. The imaging assembly 310 omits a flexible substrate in the transition region 210. Rather, the imaging assembly includes a plurality of electrical wires 316 that allow electrical signals to the exchanged between the transducers 212 and the controllers 206A, 206B. The transducers 212 can be formed on a flexible substrate, and the controllers 206A, 206B can be formed on a different flexible substrate. The electrical wires 316 can be electrically and/or mechanically coupled to both the flexible substrates and extend therebetween.

Implementing the electrical wires 316 reduces the length of the imaging assembly 310 that rigid and susceptible to kinking when the intravascular device 302 is moved through a lumen within the body of a patient. A flexible member 256 is disposed between the transducers 212 and the controllers 206A, 206B in the transition region 210. The flexible member 256 can be a tubular or cylindrical component. Advantageously, the flexible member 256 can be formed of a material than has a relatively high degree of flexibility than the transducer region 204 and the controller region 208. For example, the flexible member 256 can be formed of a material with a greater degree of flexibility than the transducer region 204 and/or the controller region 208. Accordingly, the transition region 210, formed of the flexible member 256, has a greater degree of flexibility compared to when a single substrate having conductive traces extends continuously between the controllers 206A, 206B and the transducers 212. Thus, the imaging device 302 can more easily traverse tortuous vasculature without risk of kinking.

The imaging assembly 310, including both the transducers 212 and the controllers 206A, 206B are disposed at a distal portion 304 of the imaging device 302. As described with respect to FIGS. 4B and 4C, the controllers 206A, 206B can be alternatively disposed at a central portion or a proximal portion of the imaging device 302. The plurality of electrical wires 316 extends between the transducers 212 and the controllers 206A, 206B.

The imaging device 302 can include a proximal outer member 254 and a proximal inner member 258. The proximal outer member 254 is coupled to the flexible substrate including the controllers 206A, 206B. The proximal inner member 258 can be positioned within the proximal outer member 254. The proximal inner member 258 is coupled to a support member 230 that may extend only under the distal portion 304 of the imaging assembly 310. The proximal outer member 254, flexible member 256, and the proximal inner member 258 can be formed of material(s), such as plastic(s) or polymer(s), having a high degree of flexibility. In some embodiments, the proximal outer member 254 and/or the proximal inner member 258 can be the flexible elongate member 122 that extends from the proximal portion of the imaging device 102, such as the PIM connector 114, to the scanner assembly 110. The proximal outer member 254 and/or the flexible member 256 abut and are in contact with the substrate of the controllers 206A, 206B and/or the transducers 212. A distal member 252 is coupled to the distal portion of the support member 230. The distal member 252 can be a flexible component that defines a distal most portion of the imaging device 102. For example, the distal member 252 is positioned around the distal flange 232. The distal member 252 can abut and be in contact with the stand 244 and the substrate on which the transducers 212 are formed. The distal member 252 can be the distal-most component of the imaging device 102.

One or more adhesives can be disposed between various components at the distal portion of the imaging device 302.

For example, one or more of the substrates on which the controllers 206A, 206B and the transducers 212 are formed, the support member 230, the distal member 252, the flexible member 256, the proximal inner member 258, and/or the proximal outer member 254 can be coupled to one another via an adhesive.

In some embodiments, the electrical wires 316 that connect the ultrasound transducers 212 to the controllers 206 are disposed within the flexible elongate member. For example, the electrical wires 316 are positioned within the circumference of the flexible member 256. In some embodiments, the electrical wires 316 are positioned within the imaging device 302 between the flexible member 256 and the proximal inner member 258. The electrical wires 316 facilitate electrical communication between the controllers 206A, 206B and the transducers 212. The conductors 218 facilitate electrical communication between the computing device 106 (FIG. 1) and the imaging assembly 310. The conductors 218 can extend within the flexible elongate member between the connector 114 (FIG. 1) at the proximal portion of the imaging device and the controllers 206A, 206B.

The support member 230 can be composed of a metallic material, such as stainless steel, or non-metallic material, such as a plastic or polymer as described in U.S. Provisional Application No. 61/985,220, "Pre-Doped Solid Substrate for Intravascular Devices," filed Apr. 28, 2014, the entirety of which is hereby incorporated by reference herein. The support member 230 can be ferrule. The support member 230 can define a lumen 236 extending longitudinally. The lumen 236 is in communication with the guide wire exit port 116 and is sized and shaped to receive the guide wire 118 (FIG. 1). The support member 230 can be manufactured accordingly to any suitable process. For example, the support member 230 can be machined, such as by removing material from a blank to shape the support member 230, or molded, such as by an injection molding process. In some embodiments, the support member 230 may be integrally formed as a unitary structure, while in other embodiments the support member 230 may be formed of different components, such as a ferrule and stands 244, that are fixedly coupled to one another.

Stands 244 that extend vertically are provided as a backing for the support member 230. The stands 244 elevate and support the distal portion of the flexible substrate 214 (FIGS. 2 and 3). The stands 244 can have the same outer diameter or different outer diameters. To improve acoustic performance, any cavities between the flexible substrate 214 (FIGS. 2 and 3) and the surface of the support member 230 are filled with a backing material 246. The liquid backing material 246 can be introduced between the flexible substrate 214 (FIGS. 2 and 3) and the support member 230 via passageways 235 in the stands 244. In some embodiments, suction can be applied via the passageways 235 of one of the stands 244, while the liquid backing material 246 is fed between the flexible substrate 214 (FIGS. 2 and 3) and the support member 230 via the passageways 235 of the other of the stands 244. The backing material can be cured to allow it to solidify and set. In various embodiments, the support member 230 includes more than two stands 244, only one of the stands 244, or neither of the stands.

The support member 230 can be substantially cylindrical in some embodiments. Other shapes of the support member 230 are also contemplated including geometrical, non-geometrical, symmetrical, non-symmetrical, cross-sectional profiles. Different portions the support member 230 can be variously shaped in other embodiments. In some embodiments, an inner diameter of the support member 230 (e.g., the diameter of the lumens 236 and 238) can correspondingly increase or decrease as the outer diameter changes. In other embodiments, the inner diameter of the support member 230 or diameter of the lumen 238 remains the same despite variations in the outer diameter.

Figure 4B:
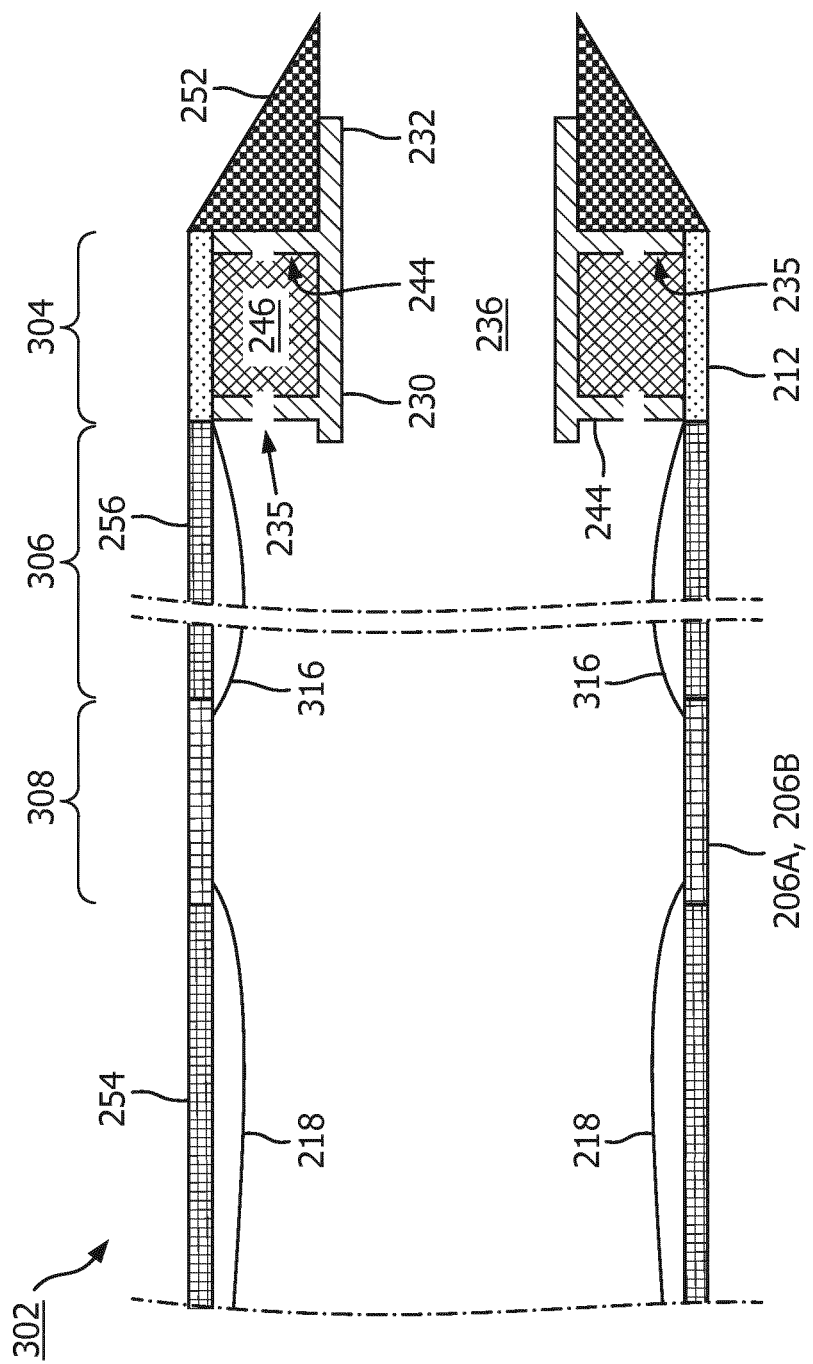
FIG. 4B is a diagrammatic cross-sectional side view of an intravascular device including an imaging assembly, according to aspects of the present disclosure.

FIGS. 4B and 4C show the diagrammatic cross-sectional side views of the intraluminal or intravascular device 302. In the embodiment of FIG. 4B, the controllers 206A, 206B are disposed at a central portion 306 of the imaging device 302. The plurality of electrical wires 316 extend from the controllers 206A, 206B at the central portion 306 to the transducers 212 at the distal portion 304. In the embodiment of FIG. 4C, the controllers 206A, 206B are disposed at a proximal portion 308 of the imaging device 302. The plurality of electrical wires 316 extend from the controllers 206A, 206B at the proximal portion 308 to the transducers 212 at the distal portion 304. The embodiments of the FIGS. 4B and 4C separate the portions of the imaging device 302 that include stiff components, such as the transducers 212 and the controllers 206A, 206B, by the flexible member 256 such that the imaging device 302 can easily traverse tortuous vasculature without kinking. FIGS. 4B and 4C omit the proximal inner member 258 shown in FIG. 4A. As described in FIGS. 8A-8D, an interior of the intravascular device 302 can be arranged to include the plurality of electrical wires 316, as well as other components such as steering wires, a guide wire, a therapeutic device, etc.

Figure 5:
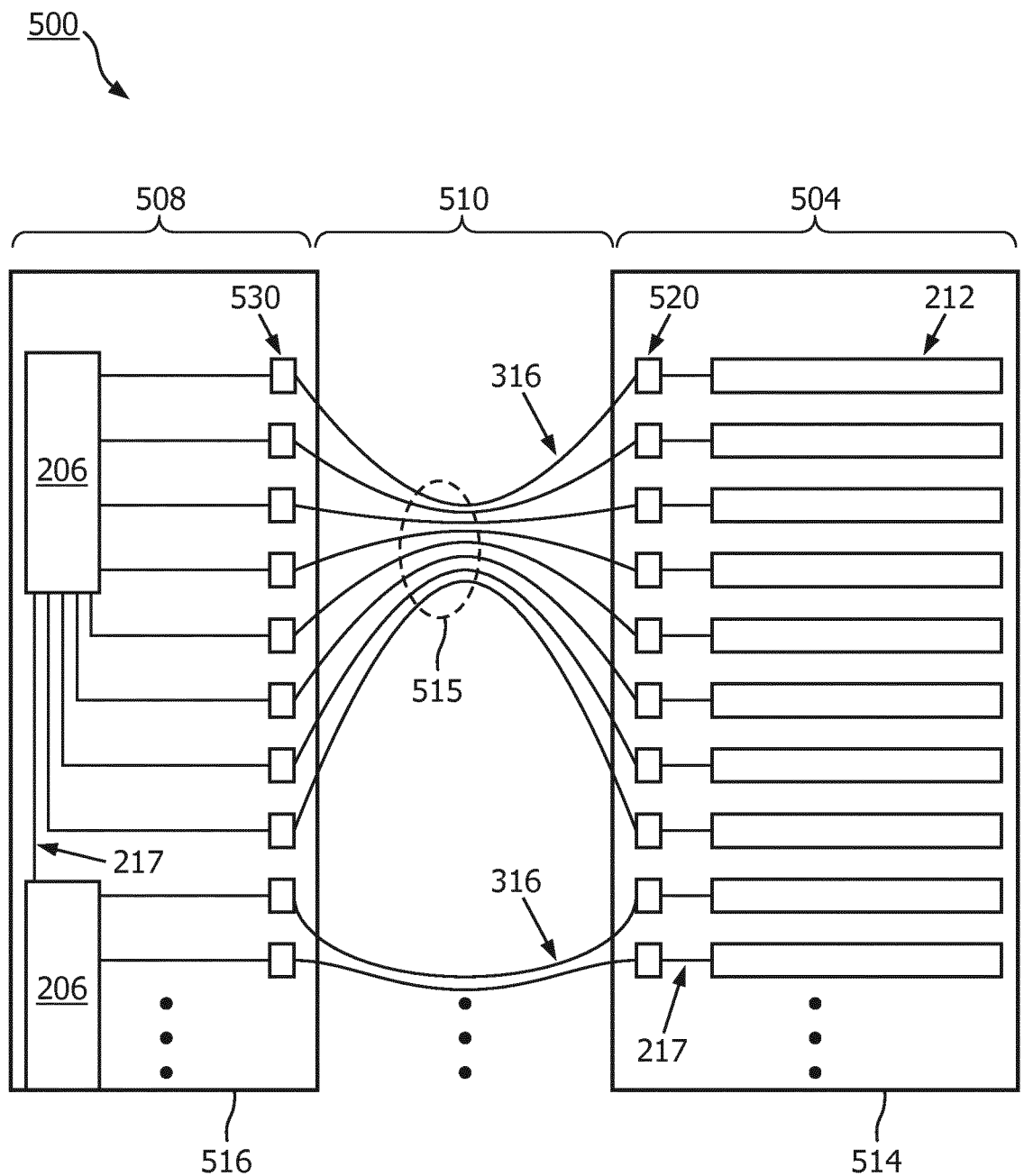
FIG. 5 is a diagrammatic top view of a scanner assembly including bundle of electrical wires, showing a bundle of wires, according to aspects of the present disclosure.

FIG. 5 is a diagrammatic top view of a scanner or imaging assembly 500, including a plurality of electrical wires 316 in a flat configuration, according to aspects of the present disclosure. The imaging assembly 500 can be implemented in the intraluminal or intravascular devices 102, 302, described herein. FIG. 5 illustrates only a portion of the controllers 206, electrical wires 316, and transducers 212. It is understood that the imaging assembly 500 can include more controllers 206, electrical wires 316, and transducers 212 than illustrated in FIG. 5. For example, one bundle 515 of wires 316 associated with a single controller 206 and multiple respective transducer elements 212 are shown. It is understood that the imaging assembly 500 can include multiple bundles 515 respectively associated with multiple controllers 206 and the corresponding transducer elements 212.

As noted, the scanner assembly 500 and the flexible substrate 514 can be similar to scanner assembly 110 and the flexible substrate 214. The scanner assembly 500 may include a transducer region 504 having a plurality of transducers 212 at a distal portion and a controller region 508 having plurality of controllers 206 at a proximal portion. The transducers 212 are formed on the flexible substrate 514, and the controllers 206 are formed on the flexible substrate 516. The flexible substrates 514, 516 are spaced from one another. A transition region 510 having a plurality of conductive electrical wires 316 extending in a central portion between the distal and proximal portions facilitates communication between the plurality of transducers 212 and a plurality of controllers 206.

In some embodiments, the electrical wires 316 each extend individually between the controllers 206 and the transducers 212. In other embodiments, the multiple electrical wires 316 are grouped or bundled together into one or more bundles. In that regard, each bundle may be surrounded by a sheath, insulation member, or other suitable conduit. The transition region 510 comprises a bundle 515 that include multiple electrical wires 316. For example, each bundle 515 can include two or more electrical wires 316. In an example each bundle 515 between four wires and sixteen wires, for example. In some embodiments, the transition region 510 can include two or more bundles 515. In some examples, the plurality of bundles 515 extend between the flexible substrate 514 and the flexible substrate 516 and couple the plurality of transducers 212 to the plurality of controllers 206. In some examples, each bundle 515 is coupled to a separate controller 206 of the plurality of controllers.

In some embodiments, the quantity of electrical wires 316 equals the quantity of ultrasound transducer elements 212. For example, the imaging assembly 500 can include sixty-four transducers 212 and sixty-four wires 316. In some examples, each bundle 515 includes sixteen wires 316. The imaging assembly 500 can include four bundles 515 in such embodiments. In another example, each bundle 515 includes eight wires 316, and there are eight bundles 515 such that each bundle 515 is coupled to a separate controller 206. The imaging assembly 500 can include eight ASIC controllers 206B for controlling the ultrasound transducers 212. The imaging assembly 500 can also include a separate ASIC master controller 206A for controlling the ASIC controllers 206B. The controllers 206A, 206B can be in electrical communication via conductive traces 217 formed in the substrate 516.

The two or more bundles 515 can be parallel or non-parallel. One or more bundles of the transition region 510 may extend at an oblique angle relative to the transducer and controller regions 504, 508. In some examples, the electrical wires 316 can be microwires with a small diameter. For example, each electrical wire 316 can have a diameter between 40 AWG and 52 AWG. Each electrical wire 316 can comprise a conductor surrounded by insulation.

In some embodiments, each electrical wire 316 can carry electrical signals between a single controller 206 and a single transducer 212. In some embodiments, each controller 206 sends and receives signals to multiple transducers 212 via respective electrical wires 316. For example, each controller may be associated with between four and sixteen wires, such as eight wires. In that regard, the bundles 515 can be associated with respective controllers 206. In some examples, a bundle 515 of electrical wires 316 includes eight electrical wires that couple ultrasound transducers 212 to a controller 206. Each transducer 212 can be associated with a single electrical wire 316, for example.

The imaging assembly 500 can include connection pads or locations 520 and 530. The connection pads 520, 530 are electrically conductive members formed in the substrates 514, 516. The connection pads 520, 530 are in electrical communication with the transducers 212 and the controllers 206 via conductive traces 217 formed in the substrates 514, 516. One end of the electrical wire 316 can be electrically and mechanically coupled to the connection pad 520 associated with the transducer 212. The opposite end of the electrical wire 316 can be electrically and mechanically coupled to the connection pad 530 associated with the controller 206. For example, the electrical wire 316 can be soldered or welded to the connection pads 520, 530. Thus, electrical communication between the controller 206 and the transducer 212 is established.

As described with respect to FIGS. 4A, 4B, and 4C, the transition region 210, 510 can have any suitable length such that the controllers 206 can be at the distal portion of the flexible elongate member 122 proximate to the ultrasound transducers, in the central portion of the flexible elongate member, or at the proximal portion of the flexible elongate member. For example, the length of the transition region 510 can be between approximately 1 cm and approximately 150 cm, for example.

Figure 6:
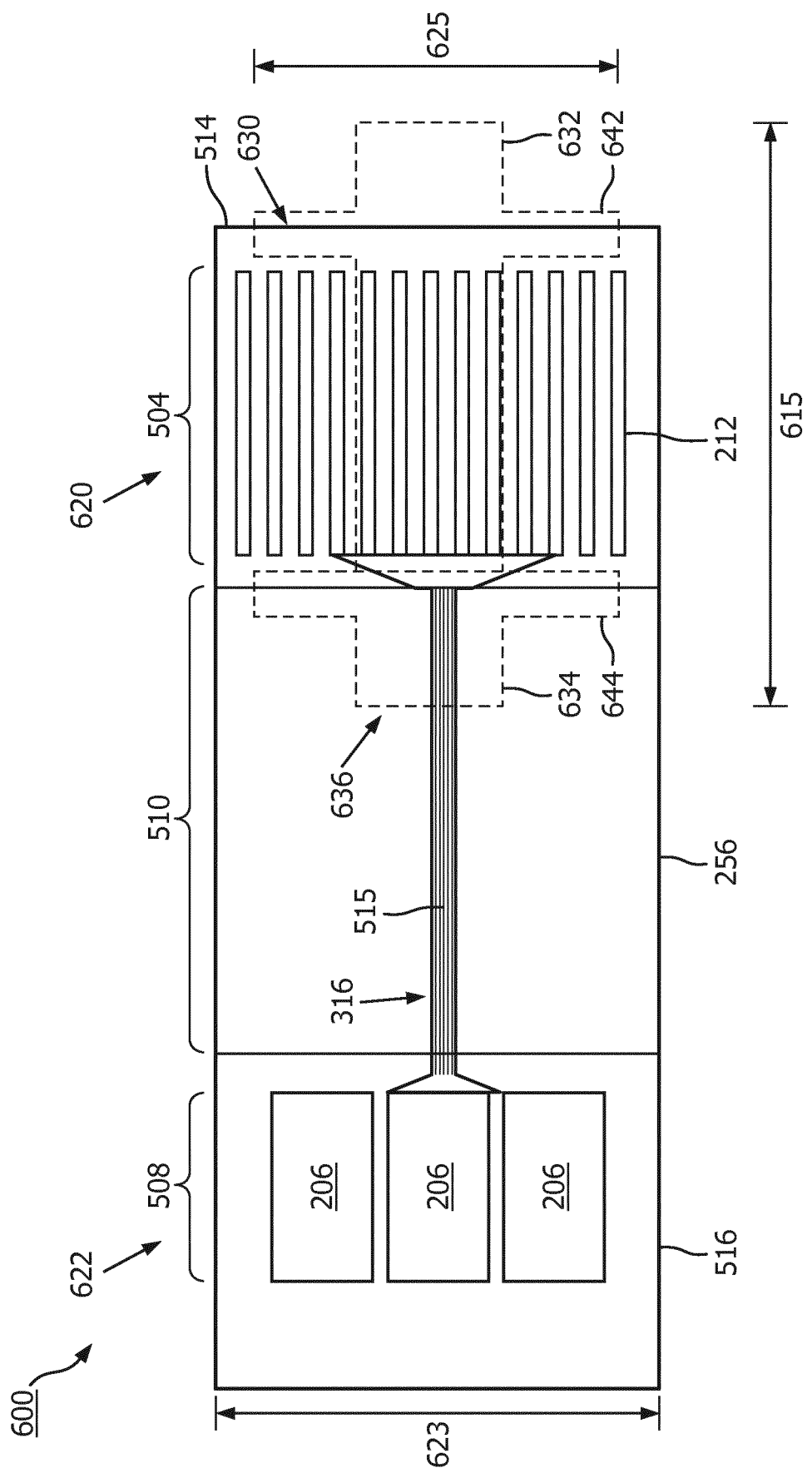
FIG. 6 is a diagrammatic side view of a scanner assembly, according to aspects of the present disclosure.
Figure 7:
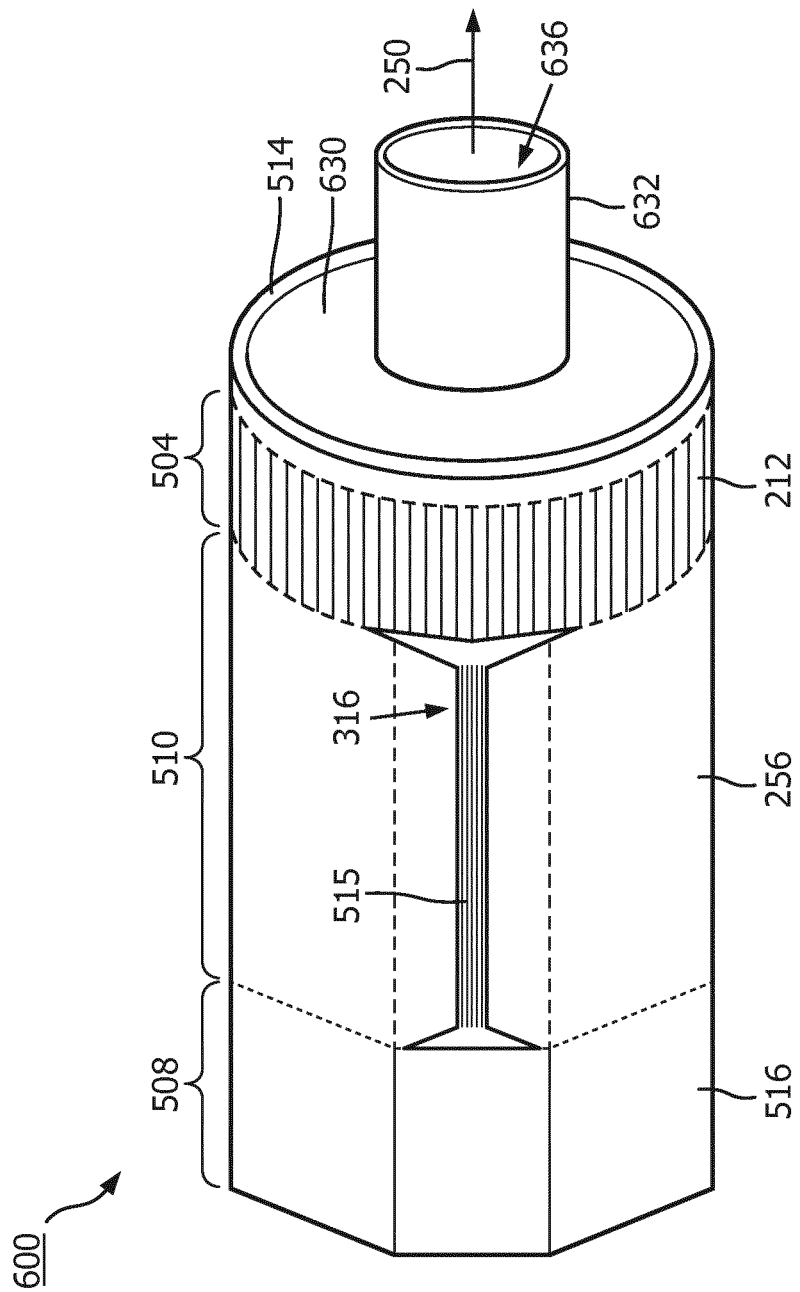
FIG. 7 is a diagrammatic side view of a scanner assembly in a rolled configuration, including a bundle of wires, according to aspects of the present disclosure.

FIGS. 6 and 7 are diagrammatic views of a scanner assembly 600, including a bundle 515 of electrical wires 316 according to aspects of the present disclosure. FIG. 6 illustrates a side view, and FIG. 7 illustrates a perspective view. The imaging assembly 600 illustrates an exemplary embodiment including the substrate 514 having transducer elements 212, the substrate 516 having controllers 206, and flexible member 256 extending between the substrate 514 and the substrate 516. The proximal portion 622 of the imaging assembly 600 includes the controller region 508. The distal portion 620 of the imaging assembly 600 includes the transducer region 504. The flexible substrate 514 is disposed in a rolled or cylindrical configuration around the support member 630. The support member component 630 is positioned remote from the controller region along a length of the intraluminal imaging assembly 600. For example, the distal support member 630 may be positioned relatively more distally along the length of the intraluminal imaging assembly 600 than the proximal portion 622. While rectangular flexible substrates 514, 516, wrapped in cylindrical configurations, are shown and described with respect to FIGS. 6 and 7, it is understood that any suitable shapes can be implemented in the imaging assembly 600. For example, the flexible substrates 514, 516 and/or flexible member 256 can have a non-rectangular shape, including one or more cutouts.

The support member 630 is similar to the support member 230 in some aspects. The support member 630 can have a generally cylindrical shape with a substantially circular or ellipsoidal profile. The support member 630 can have any other suitable shape in different embodiments, with a non-circular, polygonal cross-section. The support member 630 may include a distal flange 632, a proximal flange 634. The support member 630 can also include a distal stand 642 and a proximal stand 644. A central body portion of the support member 630 extends between the distal and proximal stands 642, 644. The transducer region 504 of the flexible substrate 514 is positioned around the support member 630 in contact with the stands 642, 644 and radially spaced from the central body portion. The stand 642 and/or stand 644 can include one or more passageways to allow introduction of an acoustic backing material into the space between the flexible substrate 514 and the central body portion of the support member 630. The support member 630 includes lumen 636. The lumens 636 can be sized and shaped to accommodate a flexible, inner, proximal member (e.g., proximal member 258 of FIG. 4A), a guide wire, and/or other suitable component. The support member 630 can have a height, width, and/or diameter 625 between approximately 0.026" and approximately 0.131", for example. A length 615 of the support member 630 can be between approximately 0.5 mm to approximately 2.0 mm, for example. The length 615 of the support member 630 can be selected based on the length of the transducer element 212 in some embodiments. The length of the transducer element 212 can be 1 mm in some embodiments.

The proximal portion 622 and/or the distal portion 620 of the imaging assembly 600 can have a height or width 623 between approximately 0.026" and 0.131", for example. The dimensions of the support members 630 and substrates 514, 516 can be selected such that the intraluminal device has a diameter between approximately 2 Fr and approximately 10 Fr, for example.

The arrangement of FIGS. 6 and 7 advantageously improves the flexibility of the imaging assembly 600 by reducing the length of the more rigid support member 630 and limiting the support member to the distal portion 620 under the ultrasound transducers 212. That is, the support member 630 can be aligned longitudinally within the transducers 212 and need to extend through the transition region 510 and the controller region 508. In some extant imaging assemblies, the rigid support member extends along the length from the controller region 508, through the transition region 510, and to the transducer region 504. The one or more bundles 515 of electrical wires 316 extending in the transition region 510 between the ultrasound transducers 212 and the controllers 206 and the flexible member 256 allowable for greater flexibility in the transition region 510. Accordingly, the imaging assembly 600 can bend more easily, without kinking, while the imaging assembly 600 traverses lumens within the patient body. FIGS. 6 and 7 illustrate one bundle 515 of wires 316 associated with a single controller 206 and multiple respective transducer elements 212. It is understood that the imaging assembly 600 can include multiple bundles 515 respectively associated with multiple controllers 206 and the corresponding transducer elements 212.

Figure 8A:
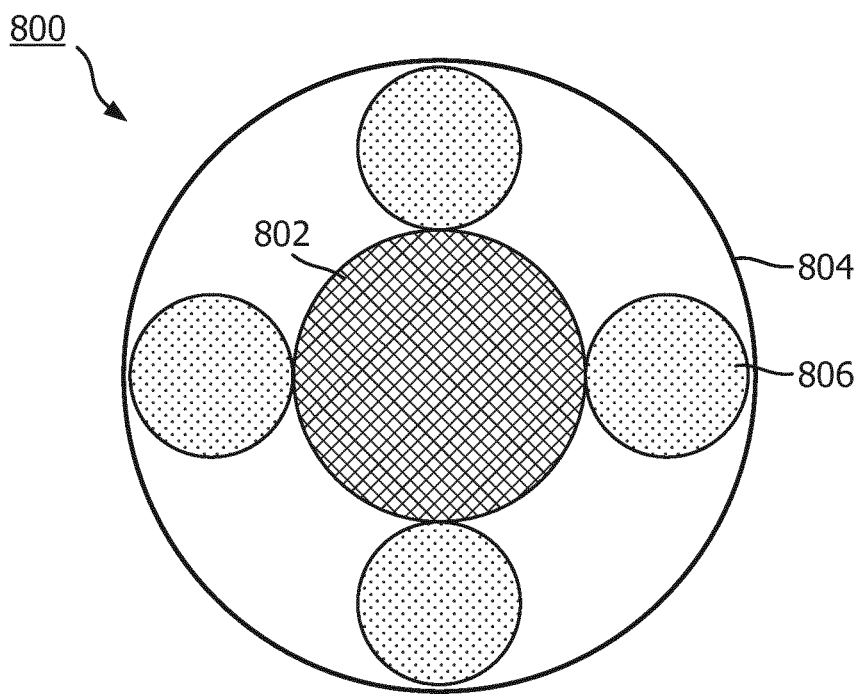
FIG. 8A is a cross-sectional view of an intravascular device along section line 8-8 in FIG. 4C, according to aspects of the present disclosure.

FIGS. 8A, 8B, 8C, and 8D are cross-sectional images of an imaging or scanner assembly along section lines 8-8 of FIG. 4C, according to aspects of the present disclosure. The embodiments 800, 830, 850, and 870 of the imaging assembly show a boundary 804, one or more lumens 802 inside the scanner assembly 110, and multiple bundles 806 of electrical wires 316. The lumen 802 may be formed by a tubular component within the flexible elongate member. The boundary 804 may be representative of a surface of the flexible elongate member 122 of the imaging device 102 (FIG. 1). For example, the boundary 804 can be representative of the flexible member 256 in some embodiments (FIG. 4C). FIGS. 8A, 8B, 8C, and 8D illustrate exemplary internal structures of the imaging device 102. As shown in FIG. 8A, the lumen 802 and the bundles of wire 806 extend parallel to the longitudinal axis 250 of the flexible elongate member 122. The lumen 802 is radially positioned within the center of the flexible elongate member. The lumen 802 can be a lumen of the proximal inner member 258 (FIG. 4A) in some embodiments. The bundles of wire 806 are arranged in an annular configuration around the longitudinal axis 250 of the flexible elongate member. In some examples, the bundles 515 are evenly spaced around a circumference of the flexible elongate member 122. Generally, the lumen 802 can be sized and shaped to accommodate and/or enclose any suitable component. For example, a guide wire, a steering wire, a therapeutic device, such as a needle, ablation tip, etc. can extend through the lumen 802.

Figure 8B:
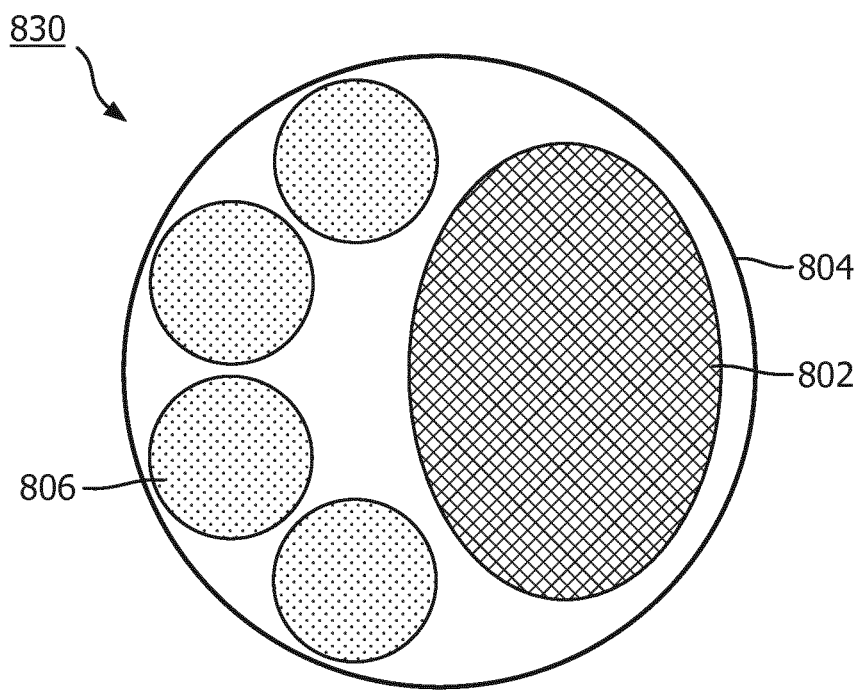
FIG. 8B is a cross-sectional view of an intravascular device along section line 8-8 in FIG. 4C, according to aspects of the present disclosure.

As shown in FIG. 8B, the lumen 802 and the bundles of wire 806 extend parallel to the longitudinal axis 250 of the flexible elongate member. In contrast to FIG. 8A, the bundles 806 of electrical wires 316 are radially offset from central longitudinal axis such that the bundles 806 are positioned at one side of the flexible elongate member. For example, the plurality of bundles 806 is disposed a clustered configuration at a first side of the longitudinal axis 250 of the flexible elongate member 122. The lumen 802 is positioned at an opposite, second side of the flexible elongate member.

Figure 8C:
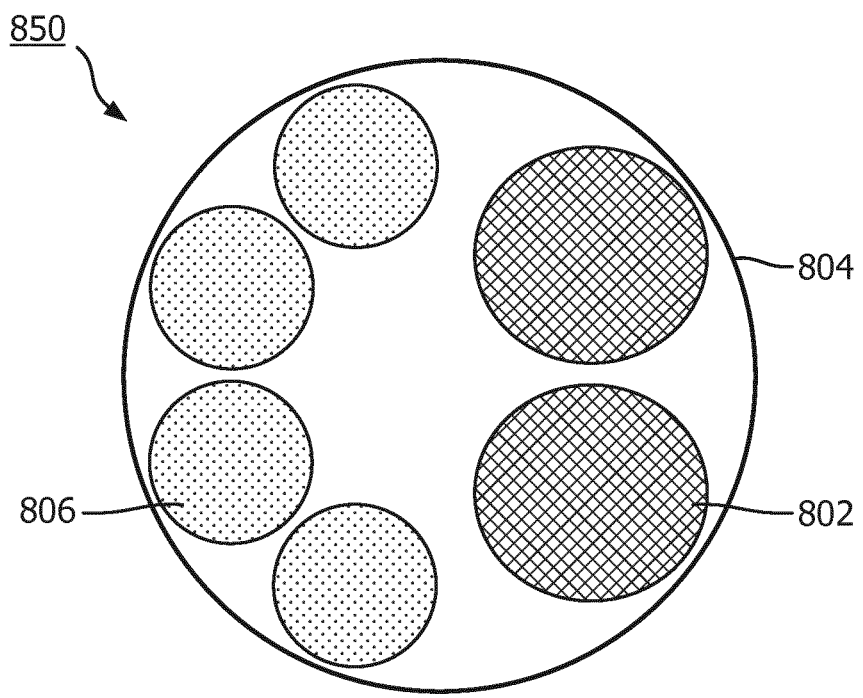
FIG. 8C is a cross-sectional view of an intravascular device along section line 8-8 in FIG. 4C, according to aspects of the present disclosure.

FIG. 8C is similar to the embodiment shown in FIG. 8B. The embodiment 850 of the flexible elongate member includes two lumens 802, both in the opposite side of the bundles of wire 806 with respect to the central longitudinal axis.

Figure 8D:
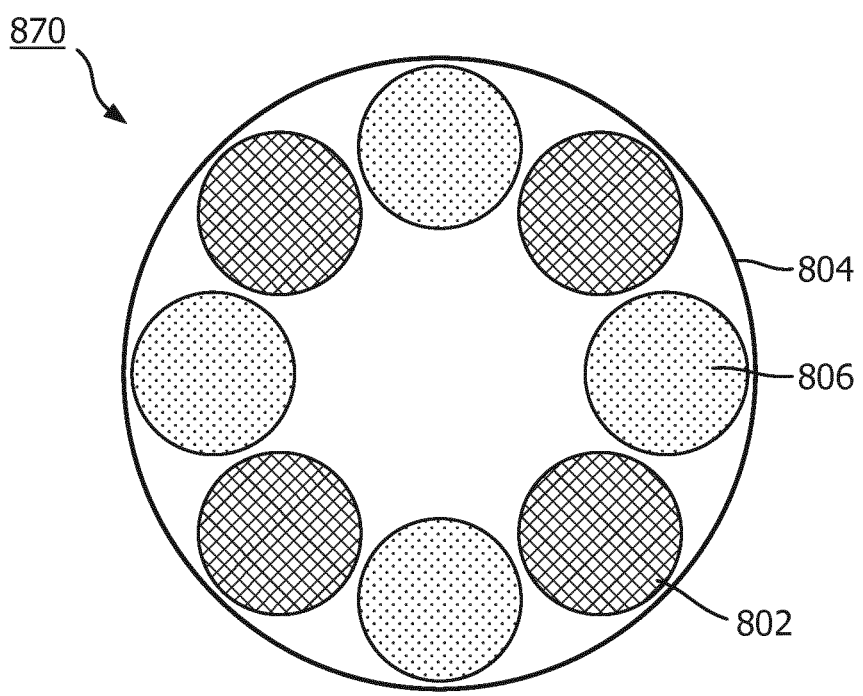
FIG. 8D is a cross-sectional view of an intravascular device along section line 8-8 in FIG. 4C, according to aspects of the present disclosure.

As shown in FIG. 8D, multiple lumens 802 and multiple bundles of wire 806 all extended in parallel to the longitudinal axis 250 of the flexible elongate member. Both lumens 802 and the bundles of wire 806 have an arrangement around the central longitudinal axis. In some examples the bundles of wire 806 are dispose in an annular configuration around a circle or a polygon. In some embodiments, a lumen 802 is positioned in the space between the bundles 806. In some embodiments, one or more steering wires extend through the respective lumens 802 along the longitudinal axis 250. The steering wires can be configured to deflect the distal portion of the flexible elongate member 122 in response to a user actuation at the proximal end of the intravascular device 102. The steering wires may be positioned in the spaces, e.g., lumen 802, between the bundles 806.

Figure 9:
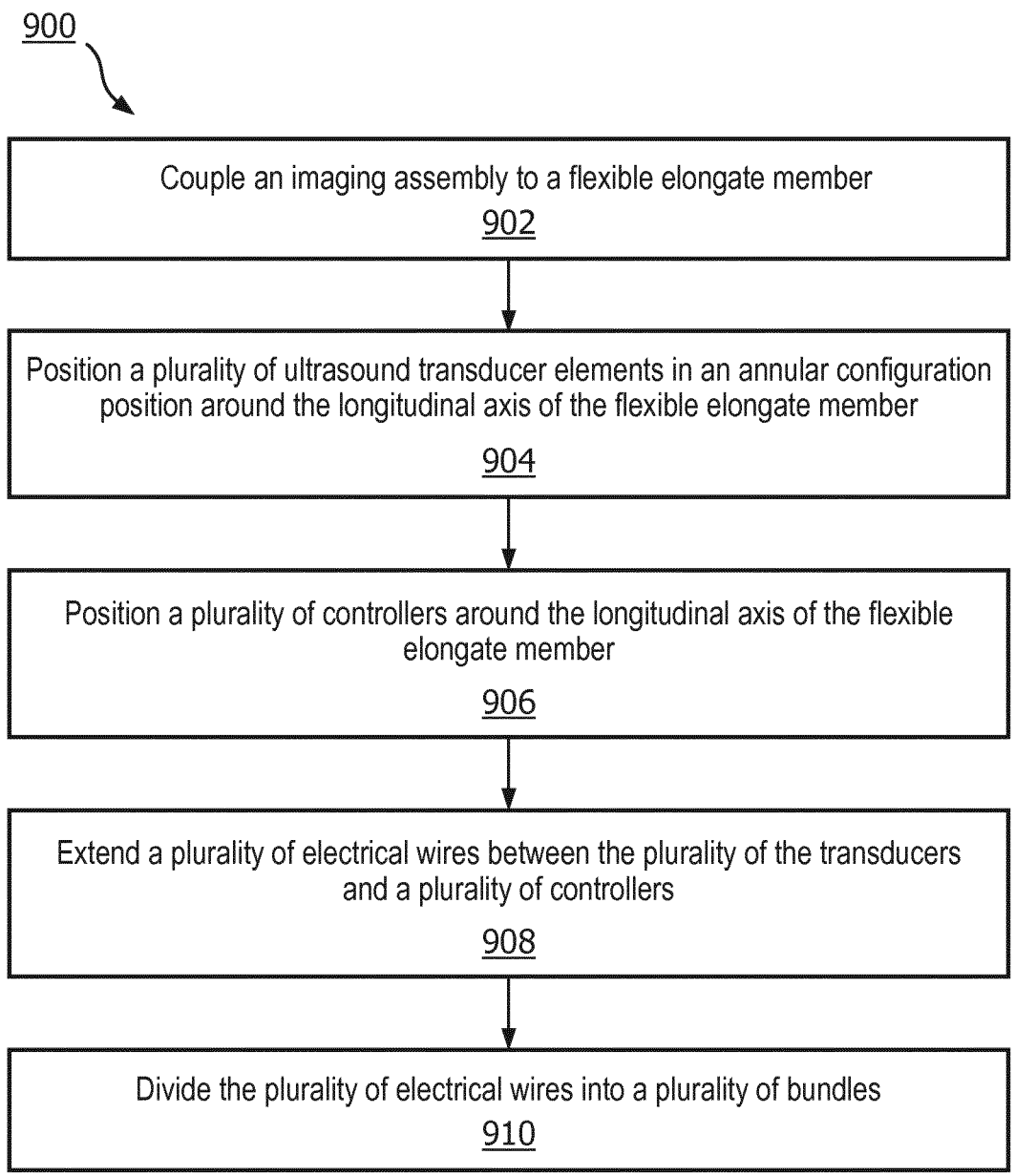
FIG. 9 is a flow diagram of a method of assembling an intraluminal imaging device, according to aspects of the present disclosure.

FIG. 9 is a flow diagram of a method 900 of assembling an intraluminal imaging device, including an imaging assembly with a support member described herein. It is understood that the steps of method 900 may be performed in a different order than shown in FIG. 9, additional steps can be provided before, during, and after the steps, and/or some of the steps described can be replaced or eliminated in other embodiments. The steps of the method 900 can be carried out by a manufacturer of the intraluminal imaging device 102.

At step 902, the method 900 includes coupling an imaging assembly to a flexible elongate member. The flexible elongate member 122 includes a proximal portion, a central portion, a distal portion, and a longitudinal axis. The flexible elongate member 122 is described with respect to FIGS. 1, 4A-4C, and 8A-8C, for example. The imaging assembly is described, for example, with respect to FIGS. 4A-7, for example.

At step 904, the method 900 includes positioning a plurality of ultrasound transducer elements in an annular configuration. As shown in FIGS. 3 and 7, the ultrasound transducers 212 are disposed around the longitudinal axis 250 of the flexible elongate member. In some examples the ultrasound transducers are dispose around a circle or a polygon. As shown in FIGS. 6 and 7, the ultrasound transducers 212 are coupled to the flexible substrate 514. The flexible substrate 514 is wrapped in a rolled or cylindrical configuration around the support member 630.

At step 906, the method 900 includes positioning a plurality of controllers around a longitudinal axis of the flexible elongate member. For example, the controllers can be positioned in an annular configuration, for example, around a circle or a polygon. As shown in FIGS. 3 and 7, the controllers 206 are disposed around the longitudinal axis 250 of the flexible elongate member. As shown in FIGS. 6 and 7, the controllers 206 are coupled to the flexible substrate 516. The flexible substrate 516 is wrapped in a rolled or cylindrical configuration around the support member 630.

At step 908, the method 900 includes extending a plurality of electrical wires between the plurality of the transducers and a plurality of controllers. As noted above with respect to FIGS. 6 and 7, for example, the ultrasound transducers 212 are coupled to the flexible substrate 514 in the transducer region 504, and the controllers 206 are coupled to the flexible substrate 516 in the controller region 508. The plurality of electrical wires extends between the controllers 206 and the transducers 212 in the transition region 510 between the transducer region 504 and the control region 508. Step 906 can include mechanically and/or electrically coupling ends of the electrical wires to the substrates 514, 516.

At step 910, the method 900 includes dividing the plurality of electrical wires into a plurality of bundles. The bundle 515 of electrical wires 316 are shown with respect to FIGS. 5-7. In some examples, an individual controller 206 may control eight ultrasound transducers 212 and the bundle 515 of electrical wires 316 includes eight electrical wires 316 extending between the controller 206 in the control region 508 over the transition region 510 to eight ultrasound transducers 212 in the transducer region 504.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intraluminal imaging device, comprising:
a flexible elongate member configured to be inserted into a first lumen within a body of a patient, the flexible elongate member comprising a longitudinal axis;
an imaging assembly coupled to the flexible elongate member, the imaging assembly comprising:
a plurality of ultrasound transducer elements;
a plurality of controllers configured to control the plurality of ultrasound transducer elements to obtain imaging data associated with the first lumen;
a first flexible substrate positioned around the longitudinal axis of the flexible elongate member, wherein the plurality of ultrasound transducer elements are disposed on the first flexible substrate such that the plurality of ultrasound transducer elements are positioned around the longitudinal axis;
a flexible tubular member disposed between the plurality of controllers and the first flexible substrate such that the flexible tubular member is separate from the first flexible substrate, wherein the flexible tubular member is more flexible than the first flexible substrate; and
a plurality of electrical wires separate from the first flexible substrate, extending between the plurality of the ultrasound transducer elements and the plurality of controllers, and configured to facilitate communication between the plurality of ultrasound transducer elements and the plurality of controllers, wherein the plurality of electrical wires are disposed inside of a space defined by the flexible tubular member.

2. The intraluminal imaging device of claim 1, wherein a quantity of the plurality of ultrasound transducer elements equals a quantity of the plurality of electrical wires.

3. The intraluminal imaging device of claim 1, wherein the plurality of electrical wires are divided into a plurality of bundles, each of the plurality of bundles comprising multiple electrical wires of the plurality of electrical wires.

4. The intraluminal imaging device of claim 3, wherein the plurality of bundles are spaced around a circumference within the flexible elongate member.

5. The intraluminal imaging device of claim 4, further comprising a steering wire configured to deflect a distal portion of the flexible elongate member, wherein the steering wire is positioned between the plurality of bundles within the flexible elongate member.

6. The intraluminal imaging device of claim 4, wherein the flexible elongate member further comprises a second lumen enclosing at least one of a guide wire or a therapeutic device, the second lumen positioned between the plurality of bundles within the flexible elongate member.

7. The intraluminal imaging device of claim 1, wherein the imaging assembly further comprises:
a second flexible substrate different from the first flexible substrate, wherein the plurality of controllers are formed on the second flexible substrate,
wherein the plurality of electrical wires extend between the first and second flexible substrates.

8. The intraluminal imaging device of claim 7, wherein the first flexible substrate and not the second flexible substrate is positioned around a support member.

9. The intraluminal imaging device of claim 1, wherein the flexible elongate member comprises a central portion and a distal portion, wherein the plurality of ultrasound transducer elements are disposed at the distal portion of the flexible elongate member, wherein the plurality of controllers are disposed at the central portion of the flexible elongate member, and wherein the plurality of electrical wires extend between the central portion and the distal portion.

10. The intraluminal imaging device of claim 1, wherein the flexible elongate member comprises a proximal portion and a distal portion, wherein the plurality of ultrasound transducer elements are disposed at the distal portion of the flexible elongate member, wherein the plurality of controllers are disposed at the proximal portion of the flexible elongate member, and wherein the plurality of electrical wires extend between the proximal portion and the distal portion.

11. The intraluminal imaging device of claim 1, wherein the plurality of electrical wires are spaced from the flexible tubular member.

12. The intraluminal imaging device of claim 1, wherein the plurality of electrical wires extend in a direction along the longitudinal axis of the flexible elongate member.

13. A method of assembling an intraluminal imaging device, comprising:
positioning a flexible substrate around a longitudinal axis of a flexible elongate member configured to be inserted into a lumen within a body of a patient, wherein a plurality of ultrasound transducer elements are disposed on the flexible substrate such that the plurality of ultrasound transducer elements are positioned around the longitudinal axis;
positioning a plurality of controllers around the longitudinal axis of the flexible elongate member;
positioning a flexible tubular member between the flexible substrate and the plurality of controllers such that the flexible tubular member is separate from the flexible substrate, wherein the flexible tubular member is more flexible than the flexible substrate; and
establishing electrical communication between the plurality of controllers and the plurality of ultrasound transducer elements by extending a plurality of electrical wires between the plurality of the ultrasound transducer elements and the plurality of controllers, wherein the plurality of electrical wires are separate from the flexible substrate, wherein the plurality of electrical wires are disposed inside of a space defined by the flexible tubular member.

14. The method of claim 13, further comprising:
coupling a first end of each electrical wire of the plurality of electrical wires to a first connection pad associated with a controller of the plurality of controllers; and
coupling a second end of each electrical wire of the plurality of electrical wires to a second connection pad associated with a transducer element of the plurality of ultrasound transducer elements.

15. The method of claim 13, further comprising:
dividing the plurality of electrical wires into a plurality of bundles, wherein each bundle of the plurality of bundles comprises multiple electrical wires of the plurality of electrical wires,
wherein the extending the plurality of electrical wires comprises extending the plurality of bundles between the plurality of ultrasound transducer elements and the plurality of controllers.

16. The method of claim 15, further comprising:
coupling each bundle of the plurality of bundles to a separate controller of the plurality of the controllers.

17. The method of claim 15, further comprising:
distributing the plurality of bundles in an annular configuration within the flexible elongate member.

18. The method of claim 17, further comprising:
extending a steering wire configured to deflect a distal portion of the flexible elongate member within the flexible elongate member between the plurality of bundles.

19. The method of claim 15, further comprising:
positioning the plurality of bundles in a clustered configuration within the flexible elongate member at a first side offset from the longitudinal axis.

20. The method of claim 19, further comprising:
extending at least one of a guide wire or a therapeutic device within the flexible elongate member on a second side opposite the first side.

21. An imaging system, comprising:
an intraluminal imaging device, comprising:
a flexible elongate member configured to be inserted into a lumen within a body of a patient, the flexible elongate member comprising a longitudinal axis;
an imaging assembly coupled to the flexible elongate member, the imaging assembly comprising:
a plurality of ultrasound transducer elements;
a plurality of controllers configured to control the plurality of ultrasound transducer elements to obtain imaging data associated with the lumen;
a flexible substrate positioned around the longitudinal axis of the flexible elongate member, wherein the plurality of ultrasound transducer elements are disposed on the flexible substrate such that the plurality of ultrasound transducer elements are positioned around the longitudinal axis;
a flexible tubular member disposed between the plurality of controllers and the flexible substrate such that the flexible tubular member is separate from the flexible substrate, wherein the flexible tubular member is more flexible than the flexible substrate; and
a plurality of electrical wires separate from the flexible substrate, extending between the plurality of the ultrasound transducer elements and the plurality of controllers, and configured to facilitate communication between the plurality of ultrasound transducer elements and the plurality of controllers, wherein the plurality of electrical wires are disposed inside of a space defined by the flexible tubular member; and
a computing device in communication with the intraluminal imaging device, wherein the computing device is configured to process the imaging data received from the intraluminal imaging device and to output the processed imaging data to a display.

* * * * *